United States Patent [19]
Wurster et al.

[11] Patent Number: 5,690,652
[45] Date of Patent: Nov. 25, 1997

[54] SURGICAL SUTURING DEVICE

[75] Inventors: Helmut Wurster, Oberderdingen; Rainer Trapp, Graben-Neudorf, both of Germany

[73] Assignee: Forschungezentrum Karlsruhe GmbH, Karlsruhe, Germany

[21] Appl. No.: 778,972

[22] Filed: Jan. 6, 1997

Related U.S. Application Data

[63] Continuation-in-part of PCT/EP95/01849 May 5, 1995.

[30] Foreign Application Priority Data

Jul. 7, 1994 [DE] Germany .................. 44 23 881.9

[51] Int. Cl.⁶ .................................................. A61B 17/04
[52] U.S. Cl. ...................... 606/144; 606/145; 606/139
[58] Field of Search .................................. 606/144, 145, 606/147, 148, 139; 112/169

[56] References Cited

U.S. PATENT DOCUMENTS 5,571,090  11/1996  Sherts ............................. 606/144
5,591,181  1/1997   Stone et al. ..................... 606/144

FOREIGN PATENT DOCUMENTS 0 535 906  9/1992  European Pat. Off. .
2 447 719  4/1976  Germany .
4 124 383  5/1992  Germany .
4 139 628  3/1993  Germany .

*Primary Examiner*—Michael Buiz
*Assistant Examiner*—Tina T. D. Pham
*Attorney, Agent, or Firm*—Klaus J. Bach

[57] ABSTRACT

In a surgical suturing device especially for endoscopic surgery, an operating mechanism is provided which includes a drive and a locking mechanism operated by a handle from which an operating rod extends to an operating mechanism which carries at its free end a suturing head comprising two jaws between which a needle with opposite needle tips and a central eye can be exchanged while being alternately locked with the two jaws, the whole procedure being controllable by a single handle.

17 Claims, 4 Drawing Sheets

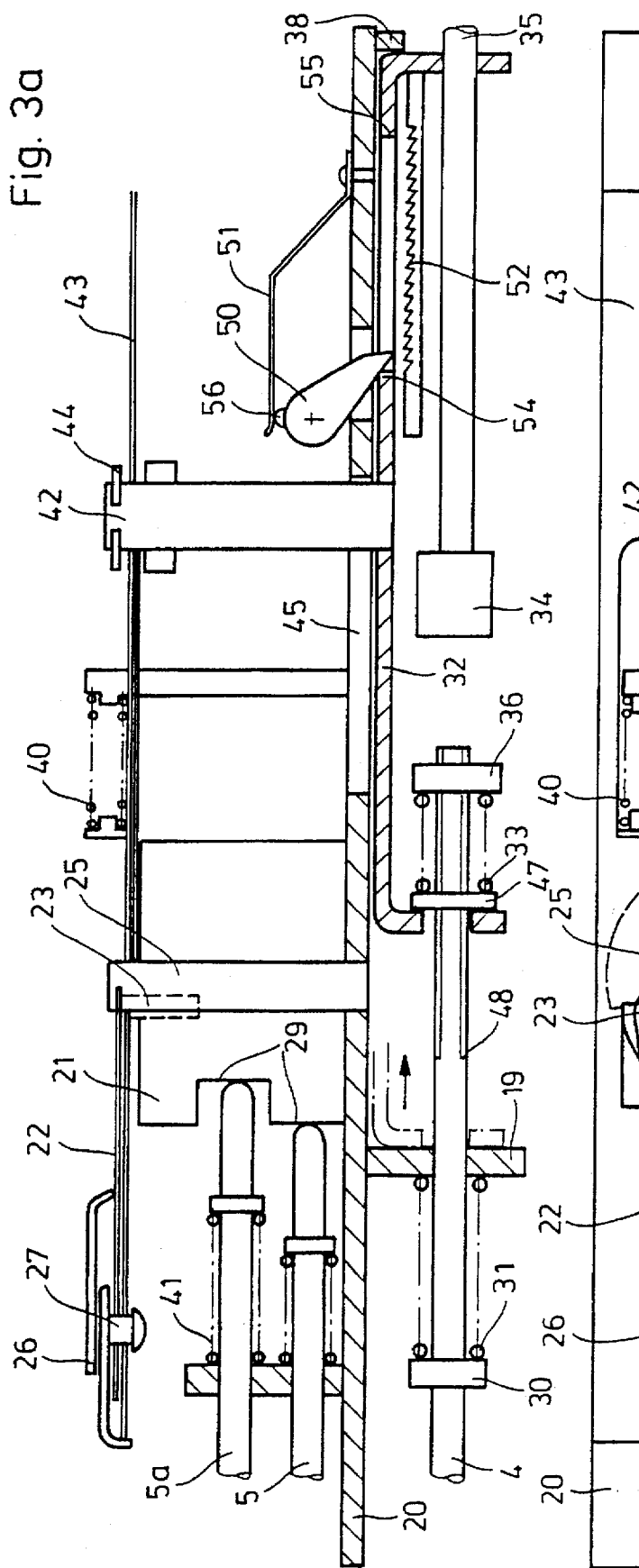
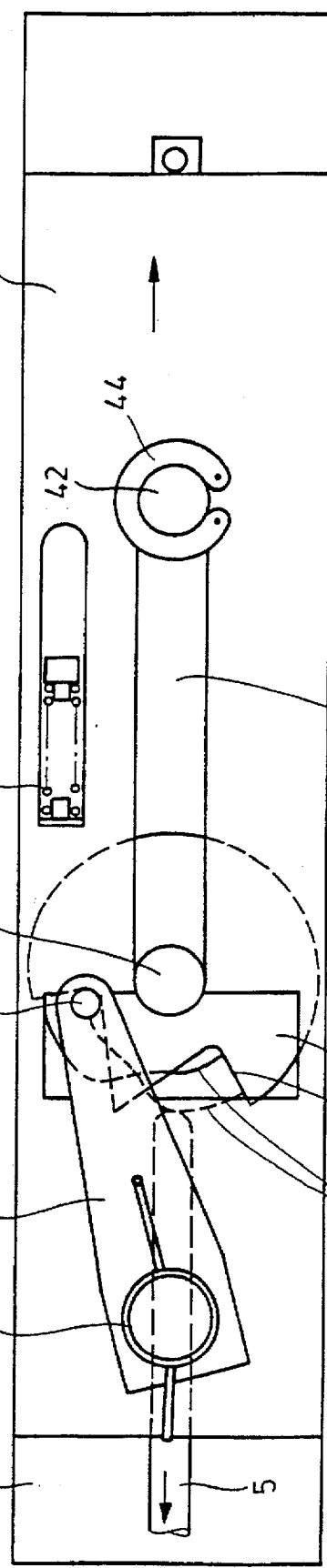
Fig. 3a
Fig. 3b

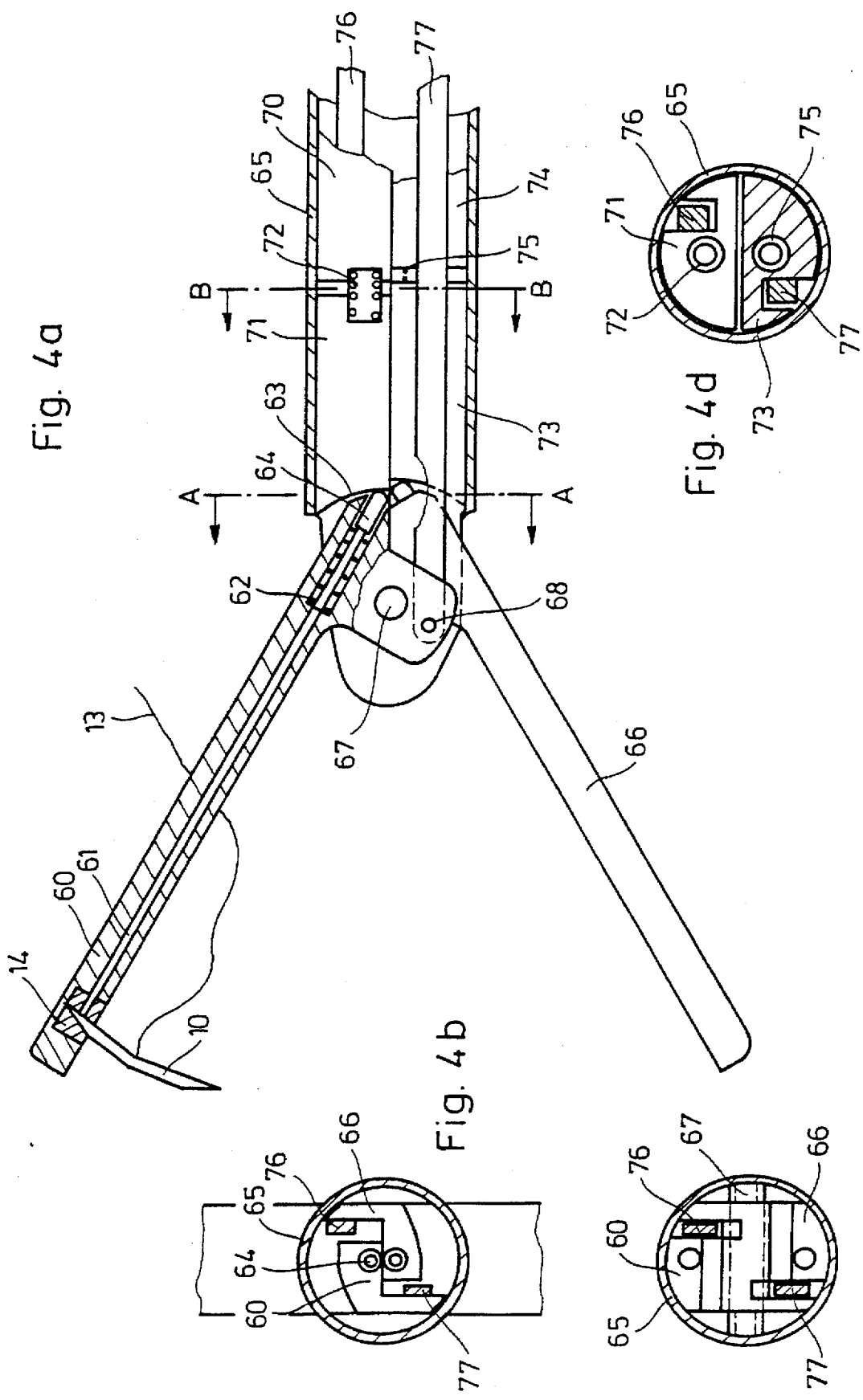

Fig. 5a
Fig. 5b
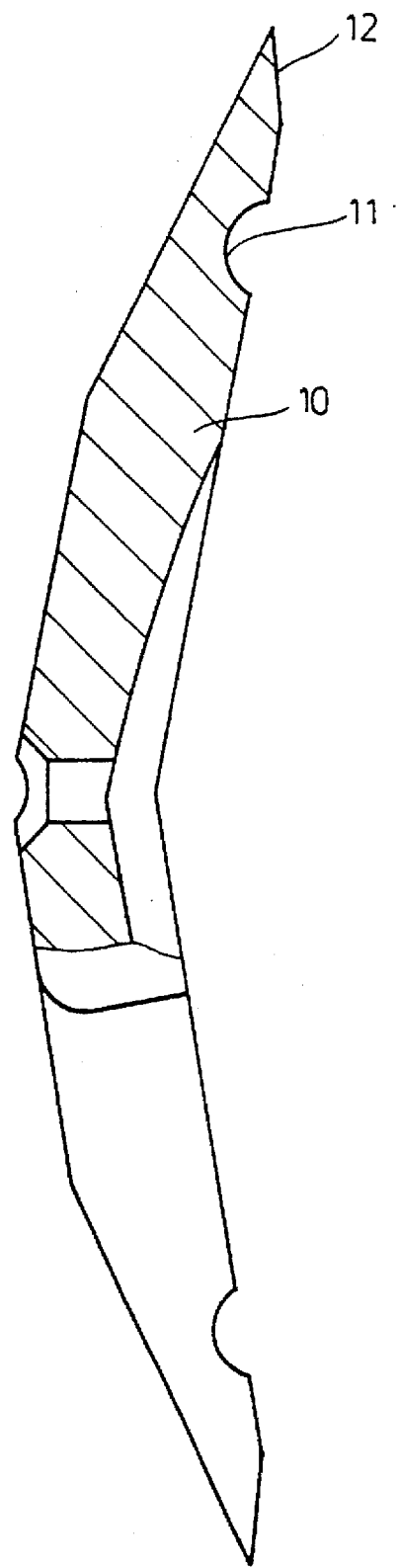
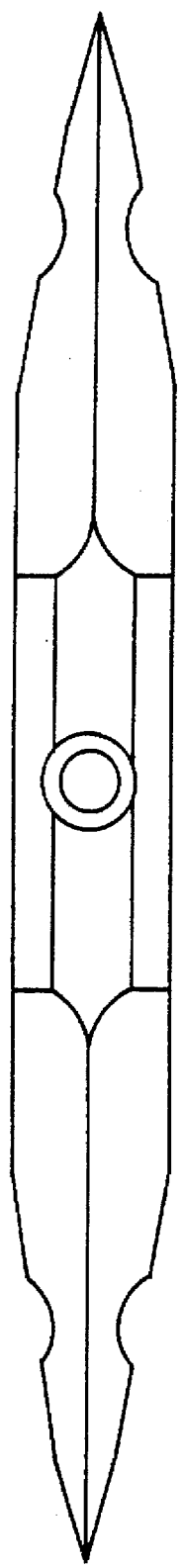

SURGICAL SUTURING DEVICE

This is a Continuation-In-Part application of international application PCT/EP95/01849 filed May 5, 1995 and claiming the priority of German application P 44 23 881.9 filed Jul. 7, 1994.

BACKGROUND OF THE INVENTION

The invention relates to a surgical suturing device especially for endoscopic surgery.

With such a suturing device, surgical sutures are made in the body of a patient with endoscopic observation, that is, through an only very small body opening or through a natural body opening.

DE 41 24 381, DE 41 24 383 and DE 41 38 628 disclose two suturing devices and an operating mechanism. The two suturing devices utilize a particular apparatus principle, that is, a suturing head with a stationary and a movable jaw part which is operated, by way of a shaft, by an external handle and a pedal switch. For the suturing procedure, a needle with an ear in the middle is transferred between the jaw parts. The needle is always firmly mounted in one of the jaw parts. Two separate operating steps are necessary in order to perform the suturing procedure. One step for the movement of the movable jaw part and the other for the engagement or the release of the needle in one of the jaw parts.

A further surgical suturing device for endoscopic surgery is disclosed in patent publication DE 42 01 337. With the instrument described therein, a bent needle is held by the force of an electromagnet which can be energized or de-energized during the movement of a bent tube portion in which the needle is received.

It always facilitates the work of a surgeon and it is therefore advantageous if the operating steps needed to operate an instrument are reduced to a minimum and if no connecting structures between the surgical instruments and peripheral equipment are needed.

It is therefore the principal object of the present invention to provide a surgical suturing device, especially for endoscopic surgery wherein the suturing procedure including the transfer of the needle can be performed with one hand.

SUMMARY OF THE INVENTION

In a surgical suturing device especially for endoscopic surgery, an operating mechanism is provided which includes a drive and a locking mechanism operated by a handle from which an operating rod extends to an operating mechanism which carries at its free end a suturing head comprising two jaws between which a needle with opposite needle tips and a central eye can be exchanged while being alternately locked with the two jaws, the whole procedure being controllable by a single handle.

A mechanical divider which transmits the movement of the handle in the ratio 2:1 is used to actuate the engagement mechanism at the stationary jaw structure so that the engagement mechanism for engaging the needle is operated only with every second movement of the handle portion. In this way, the surgeon does not need to specifically actuate a switch-over mechanism and does not need to concentrate on when to operate the handle mechanism or the foot-operated mechanism for engaging the needle.

With a continuous operation of the handle, the needle is automatically transferred from one jaw to the other so that suturing can be performed in a continuous easy procedure. The device according to the invention can be used for axial as well as radial endoscopic suturing equipment.

The needle is engaged in each jaw not by clamping means, but by a pin which is movably disposed in a jaw and has a rounded front end which is received in a groove in the needle and thereby firmly retains the needle in its guide sleeve.

Since a radial suturing device includes a needle which is curved or bent in the center, the needle must be secured in position. It has been found that a triangular needle can fulfill those requirements so that a firm seating of the needle is guaranteed. The needle which is triangular in cross-section is pointed at its ends and is slightly chamfered at its lower edge adjacent the tips to facilitate its insertion into a correspondingly shaped needle guide structure.

In another solution to the object, the needle which is engaged at one end by the pin received in the groove is not firmly engaged at the other end as shown for example in DE 41 24 381 and DE 41 24 383. Instead of being held at the opposite end in engagement with the movable jaw by way of a spring force whereby it could be disengaged by applying a predetermined pulling force, both jaws are provided with a movable pin which can be operated by a transfer mechanism which engages the needle alternatively in the respective jaw as determined by a control arrangement. In this way, it is insured that the needle is firmly engaged in the respective jaw and cannot be dislodged and lost for example, by excessive pulling on the thread. Furthermore, the needle end is not subjected to any mechanical stress when the needle is inserted into the needle guide structure since the pin engaging the needle is advanced only after the needle has been inserted into the prismatic needle engagement structure. This is achieved in that, after closing of the jaws, that is after insertion of the needle into the opposite support structure, the handle is further compressed and the switch-over mechanism is actuated thereby such that the existing engagement is released and the engagement means in the jaw into which the needle has just been inserted, is actuated. With each subsequent operation of the handle, the release and engagement of the needle in another jaw is achieved so that the needle is safely transferred from one to the other jaw and is always firmly held in one of the jaws. In this manner, the surgical suturing device is simple and safe to operate which is highly advantageous in its practical application.

By further compressing the handle after the closing of the jaws against the spring force which keeps the jaws closed, only the maximum adjusted spring pressure is effective on the jaws such that overloading of the jaws by strong compression of the handle is avoided. This is considered to be an additional advantage.

Operation of the engagement mechanism in the stationary jaw part can be achieved for example by a pin of superelastic material which can easily adapt to the jaw opening angle of 45°. For the design solution of this object, care has to be taken that the pin is not moved out of its position by the jaw movement and that the needle remains safely engaged in its position.

Two embodiments of the invention will be described below on the basis of the accompanying drawings.

BRIEF DESCRIPTION OF THE DRAWINGS

FIG. 3a is a side view of the drive and locking mechanism,

FIG. 3b is a top view of the drive and locking mechanism,

FIG. 4a shows a suturing head with two movable jaws,

FIG. 4b is a cross-sectional view taken along line A—A of FIG. 4a with the jaws open, FIG. 4c is a cross-sectional view taken along line A—A of FIG. 4a with the jaws closed, FIG. 4d is a cross-sectional view taken along line B—B of FIG. 4a, FIG. 5a is a side view of a triangular needle shown partially in cross-section, and FIG. 5b is a top view of the triangular needle.

DESCRIPTION OF PREFERRED EMBODIMENTS

Figure 1:
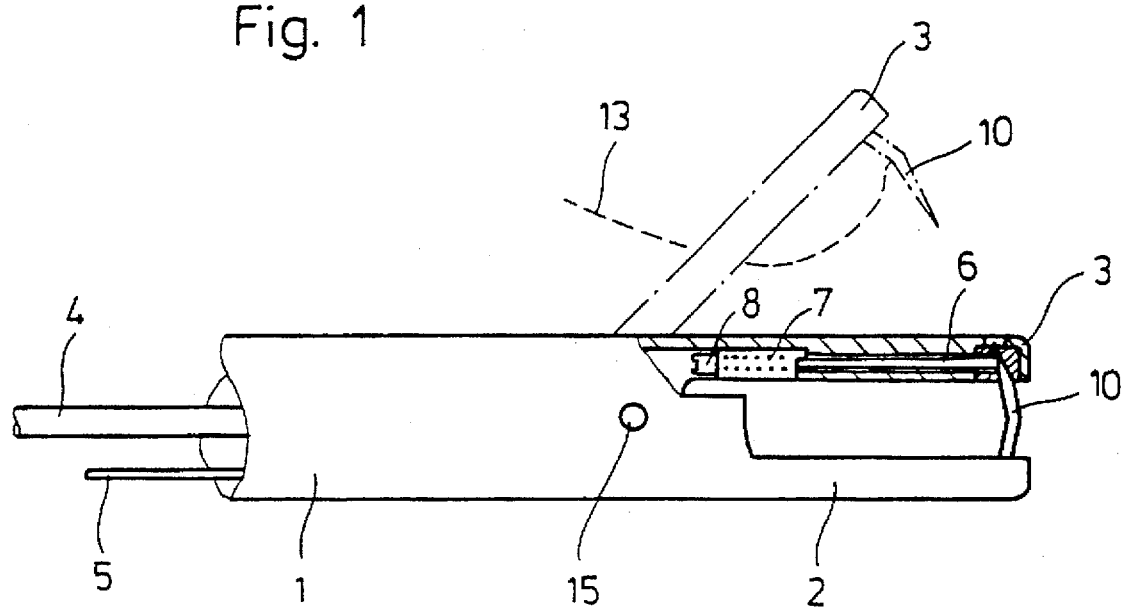
FIG. 1 shows a suturing head with a stationary and a movable jaw.

FIG. 1 shows the distal end of a surgical suturing device with a suturing head oriented in the direction of the shaft axis and also the end of the shaft tube 1. The suturing head comprises a stationary and a movable jaw 2 and 3, the movable jaw 3 being supported so that it is pivotable about the axis 15 and can be opened and closed by a push rod 4.

Figure 2:
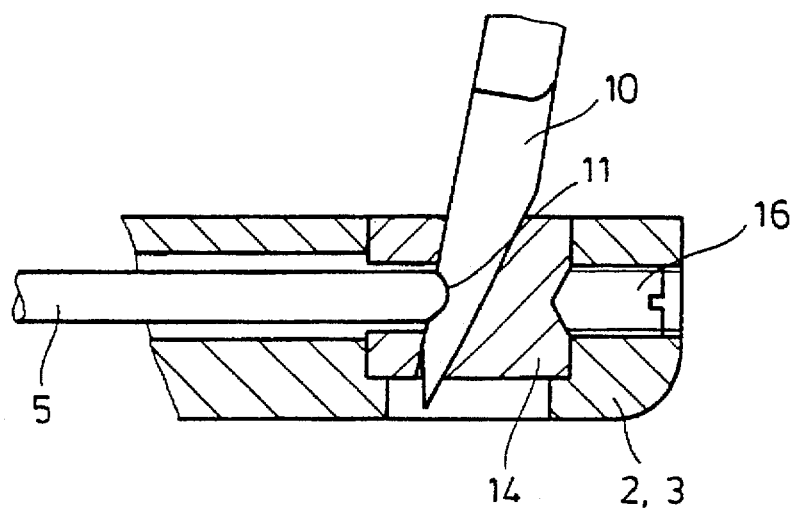
FIG. 2 shows the needle guide in the stationary jaw.

At the end of the movable jaw 3, there is a needle guide 14 as shown in FIG. 2. In contrast to the stationary jaw 2, the needle 10 is fixed in the movable jaws 3 by a pin 6 which is biased by a spring 7 into engagement with the needle 10. The spring force can be adjusted, within limits, by an adjustment screw 8. The stationary jaw includes an identical needle guide 14. However, the needle 10 is engaged in this case by way of a control rod 5 which is operated by a drive and locking mechanism.

The needle guide 14 in the jaws 2, 3 is fixed by way of a set screw 16 as shown in FIG. 2. FIG. 2 also shows how the control rod 5 or the pin 6 press the needle tip into firm engagement with the needle guide 14.

In side and top views, FIGS. 3a and 3b show the drive and locking mechanism in a state in which the handle is fully compressed.

The released-handle state, that is, the original position is shown in FIG. 3a by the angled part of the slide member 32 indicated in dash-dotted lines wherein the slide member 32 abuts the stop 19 at the base plate 20. The cooperation of the mechanical parts will be described below on the basis of these figures beginning with the released handle state. The handle shown in the drawings only schematically since it is a common component generally used with such devices. The needle 10 is inserted into the jaw 3 and is held in position by means of the pin 6 and the spring 7.

Upon compression of the handle, the slide member 32 is moved in the direction as indicated by the arrow (to the right as shown in FIG. 3a). The slide member 32 is firmly connected to the rod 35 which leads to the handle. The push rod 4 which extends through, and is guided by, the stop 19 and the angled part of the slide member, is coupled with the push rod 4 by means of the spring 33 and is also moved to the right when the handle is compressed. By this movement to the right, the movable jaw 3 pivots onto the stationary jaw 2 and the needle 10 is inserted into the free needle guide 14.

This movement to the right is also experienced by the bolt 42 which is firmly mounted on the slide member 32. It extends through the elongated hole 45 in the base plate 20 and has at its free end a plate 43 disposed on a flange and secured by way of a spring clip 44. The plate 43 is guided by the shaft 25 and, for this purpose, also has an elongated hole 46 (see FIG. 3b). The shift lever 22 is rotatably supported by the bolt 27 on the longitudinal center axis of the plate 43 so as to be rotatable in such a way that with its free end on which the shift pin 23 is disposed which extends through the plate 43, it is pivoted toward the longitudinal center line by the return force of the spring 26 if it is free to do so.

During the movement of the handle as described so far, the shift pin 23 is received as shown in FIG. 3b in the upper half of the W-shaped recess 28 of the transfer member 21 and rotates this member in the respective direction (to the right). The transfer member 21 is rotatably supported on the shaft 25. Formed on the transfer member 21 are the two cams 29 which have oppositely shaped cam surfaces. They are carried along in the respective direction of rotation and operate the control rods 5 and 5a. In the arrangement as shown, the control rods 5 and 5a move therefore in opposite directions.

By an adjustment mechanism, which is not shown but which operates by way of fine thread, the control rods 5, 5a can be adjusted in axial direction such that the needle 10 is firmly engaged by the cams when they are in locking positions. The two springs 41 at the end of the cams 29 always hold the control rods 5, 5a in contact with the respective cam 29 in any position of the transfer member 21.

In the position as shown in FIGS. 3a and 3b, the control rod 5 is pushed fully forward by the lower cam 29 (FIG. 3a) whereby the needle 10 is firmly engaged with the needle tip received in the needle guide 14 of the stationary jaw 2.

A certain position on the way to the stop 38 is maintained by a locking mechanism in the form of a ratchet structure arranged at the right end of the base plate 20. The ratchet consists of a toothed rack 52 and a locking pawl 50 which has a cam 56 by which the pawl is held in position by means of the spring 51. The toothed rack 52 is connected to the slide member 32. The locking pawl 50 is rotatably supported on the base plate 20 such that its front end extends through a cutout in the base plate 20 and engages within the slide member 32 the toothed rod 52. In this way, a return of the slide member 32 between the stops 19 and 38 is prevented.

A position change can be achieved only by further compression of the handle. This is only possible until the slide member 32 reaches, with its right-side angled end, the stop 38. Shortly before reaching this position, the edge 54 of the cutout for the pawl 50 in the slide member 32 lifts the pawl 50 out of engagement with the toothed rack 52. If the handle is now released, the slide member 32 returns to the left until its left angled end reaches the stop 19 while the pawl 50 is held in a disengaged position by the spring 51. The spring 33 expands until the washer 47 reaches the washer stop 48. The right end edge 55 of the cutout on the slide member 32 engages the pawl 50 and returns it into engagement with the toothed rack 52 in which position it is then resiliently held by the leaf spring 51. As a result, the pawl 50 has two stable positions by the action of the spring 51. It is noted however, that the ratchet mechanism is only one of several possible solutions for a bi-stable locking mechanism.

The spring 31 applies a return force to the movable jaw 3. Since the needle 10 is locked in the stationary jaw 2, however, the movable jaw cannot return because the pin 6 engages the other needle tip in the jaw 3. In order to force the movable jaw 3 open, the operating rod 35 engages with its adjustable end 34 the push rod 4 when the handle is opened whereby the needle tip is released and the needle can be pulled out of the needle guide 14 in the movable jaw 3.

The needle is now supported and locked in the stationary jaw 2 since the position of the transfer member 21 has not changed during the return of the slide member 32 and, together therewith, the plate 43 (in FIG. 3a to the left). The return movement was accomplished by the force of the spring 40 which is disposed between the plate 43 and the base plate 20.

During this movement, the shift pin 23 on the shift lever 22 slides out of the W-shaped recess 28 on the transfer member 21 and the shift lever 22 is pivoted back into alignment with the longitudinal center axis of the plate 43 under the return force of the centering spring 26. The transfer member 21 remains first in its momentary position and holds the needle tip locked in the needle guide 14 of the stationary jaw 2.

In order to now move the needle 10 through the tissue to be sutured, the handle is again compressed whereby the jaw 3 closes and pushes the tissue onto the needle 10. Upon further compression of the handle, the transfer member 21 is pivoted by the shift lever 22 in an opposite direction because the shaft pin 23 projects now into the other (lower) half of the W-shaped recess 28. As a result, the lock of the needle 10 in the stationary jaw 2 is released. At the same time, the needle 10 is locked in the movable jaw 3 by the pin 6 which is biased into engagement with the needle 10 by the spring 7.

Upon full compression of the handle, the ratchet is disabled and the jaws open again as described earlier but the needle 10 is now supported in the movable jaw 3. It can now be pulled fully through the tissue, the thread can be tensioned and a new switch can be initiated with a transfer of the needle.

FIG. 4a shows a surgical suturing device with two movable jaws 60, 66. The arrangement is further explained with reference to the cross-sectional views of FIGS. 4b, 4c and 4d.

The movable jaws 60, 66 are supported on a shaft 67 of a shaft tube 65. The jaws 60, 66 are operated by means of operating rods 76 and 77 which are linked to the jaws at the joints 68 (shown only for jaw 60). The operating rods 76,77 are combined further in the back and are actuated together by the push rod 4. Both jaws 60, 66 are identical. They each have a longitudinally extending bore receiving the locking pin 61. Near the pivot joint, the bore diameter is increased to receive a spring 62 and to provide moving space for the thickened end portion 64 of the pin 61.

The slide members 71 and 73 have front end surfaces 63 which are so formed that the positions of the pins with respect to the jaws 60 and 66 remain the same for any pivot position of the jaws. The locking position of the pins is only determined by the position of the slide members 71, 73 which engage the locking pins 61 at their ends 64. Both parts 70 and 74 are coupled with the control rods 5 and 5a which are, as explained earlier with reference to FIGS. 3a and 3b, actuated by the cams 29 in an opposite sense. In this way, the needle is alternately locked in the needle guide 14 of the jaws 60 and 66 by the handle actuation as explained earlier.

It is pointed out here, that this locking mechanism utilizing the two push rods 5 and 5a can be used for the suturing head with a stationary jaw 2 and a movable jaw 3 as described above wherein the spring locking mechanism in the movable jaw 3 as described above could be replaced by a rod control mechanism.

When the handle is released, the cams 29 remain in place. When the jaws 60 and 66 are opened, the thick end portions of the pins 64 slide along the respective front end faces 63 of the slide members 71, 73 which are so shaped that the pins 61 remain in position relative to the respective jaws 60. 66. The needle 10 therefore remains locked in the needle guide 14 in which it is engaged at that point so that it cannot fall out. The locking arrangement is actually very reliable even under relatively large loads.

If the handle is again compressed after having been fully compressed and released, further folding together of the two jaws 60 and 66 is prevented by the needle 10 after the needle tips are received in the two needle guides 14 (see earlier description). With further compression of the handle, the transfer member 21 is pivoted in the other (left) direction of rotation by the shift pin 23 of the shift lever 22 which pin now engages the other (lower) half of the W-shaped recess 28. This results in the release of the locked needle tip and the locking of the other needle tip.

If the two jaws 60 and 66 are now again opened the needle 10 with the thread threaded through the eye 13 can then be pulled fully through the tissue and a new stitch can be started.

FIG. 4b is a cross-sectional view taken along line A—A of FIG. 4a at the beginning of the suturing head with both jaws 60 and 66 opened as shown in FIG. 4a. It shows the two beginnings of the jaws 60 and 66 as well as the thickened rounded end portions 64 of the two locking pins 61. FIG. 4c shows the same cross-sectional area with the jaws 60, 66 closed. FIG. 4d finally is a cross-sectional view taken along line B—B of FIG. 4a near the end of the shaft 65 in the area of the spring 72 at the joint between the slide parts 70 and 71 and between the slide parts 73 and 74.

The handling of the instrument is simple and the needle lock arrangement is very reliable. As mentioned above, the needle may also be locked in position by spring forces. This, however, may result in the possibility that, with tough tissue, the needle may be pulled out of its resiliently engaging lock in the needle guide 14 because relatively large forces are needed for pulling the needle through such tissue. This is not easily possible if a locking mechanism is used as shown in FIGS. 4a, 4b, 4c and 4d wherein the locking pins are positively held in engagement with the needle.

The triangular needle cross-section as shown in FIG. 5a and 5b is advantageous for providing a secure needle lock. The curvature of the needle 10 which corresponds about to the circle of movement for the needle guide 14 permits a clean, ripless penetration of the tissue. The cutout 11 on the needle 10 is partially cylindrical in shape. Since the needle tip is received in the needle guide in a form-locking manner, the needle 10 cannot tip nor turn after it is locked in position by the locking pin 6 or 61.

The shape of the needle 10 as shown in FIGS. 5a, 5b with the crest-like back of the needle 10 can also be such that there is a planar area on the back side of the needle 10 and that, at the inner side of the needle 10, a crest runs from needle tip to needle tip. This is advantageous for cylindrical cutouts 11 since the needle crest then surrounds the locking pin to a greater degree whereby the needle tips are retained more securely.

The needle is preferably also provided with flat inclined areas 12 at the tips which facilitate insertion of the needle into the needle guides.

The drive and locking mechanism is not limited to the crocodile-like jaws. Suturing heads which project normally or at an inclined angle from the shaft axis can also be operated by the mechanism described. Some design modification at the transition area between the end of the shaft and the suturing head may be made of course with a different suturing head.

What is claimed is:

1. A surgical suturing device particularly for endoscopic surgery, comprising a handle mechanism and a drive and locking mechanism, a shaft connected to the drive and locking mechanism and including coupling means, a suturing head mounted at an end of said shaft and having jaws supported so as to be movable relative to each other, a needle guide disposed at the free end of each jaw, and a needle having ends with needle tips and an eye in its center and being adapted to be received and retained at its opposite ends in said needle guides by operation of said drive and locking mechanism, said drive and locking mechanism comprising a base plate, a slide member slideably supported on said base plate, a drive rod having one end rigidly connected to said slide member for operating said jaws and the opposite end connected to said handle mechanism for moving said rod and said slide member along said base plate, a pull and push rod extending between said jaws and said slide member and being engaged thereby by a spring member for pulling said rod, said rod being slideably supported on a stop projecting from said base plate and by said slide member, a toothed rack mounted on said slide member for movement therewith, a pawl pivotally supported on said base plate and extending through a cutout in said slide member into engagement with said toothed rack for holding said slide member in a particular position, means for disengaging said pawl from said toothed rack where said slide member with said toothed rack has been moved to one end position, means for holding said pawl disengaged until said slide member has moved to its opposite end position, means for returning said pawl into engagement with said toothed rack when said slide member reaches said opposite end position, a transfer structure for controlling the engagement of said needle with said jaws, including a cylindrical partially circular transfer member rotatably supported by a shaft mounted on said base plate and having a W-shaped recess formed in its circumferential surface, and cam areas for actuating a locking mechanism for locking said needle alternately in engagement with said jaw, said locking mechanism including a control plate disposed in parallel spaced relationship above said base plate and coupled, by a bolt, with said slide member for movement therewith, said bolt extending through an elongated hole in said base member to allow the movement of said bolt with said slide member, said control plate having an elongated hole receiving said shaft mounted on said base plate so as to permit movement of said control plate with said slide member, a shift lever pivotally mounted on said control plate and having a free end with a shift pin extending therefrom through a cutout in said control plate into engagement with said W-shaped recess on said transfer member, a return spring engaging said shift lever so as to bias said shift lever into a center position in longitudinal alignment with said control plate, at least one control rod having a proximal end biased into engagement with said cam on said transfer member and a distal end for reception in a recess formed in said needle adjacent the opposite ends thereof for locking said needle in said jaw, said needle being curved so as to have a shape corresponding to the path of relative movement of said jaws.

2. A surgical suturing device according to claim 1, wherein said pull and push rod has an adjustable end by which the opening angle of said jaws can be adjusted by controlling the travel length of the drive rod actuating said jaws.

3. A surgical suturing device according to claim 1, wherein a return spring is disposed between said drive rod and said stop for biasing said drive rod in a jaw opening direction, said return spring being substantially weaker than said spring member for pulling said drive rod in jaw closing direction.

4. A surgical suturing device according to claim 1, wherein said pawl has a cam projecting therefrom and a leaf spring is provided engaging said cam for biasing said pawl into engagement with said toothed rack, said cam on said pawl and said leaf spring being so arranged that said pawl is held disengaged from said toothed rack after being disengaged by said slide member in one end position of said slide member.

5. A surgical suturing device according to claim 4, wherein said spring forms with said pawl a bi-stable snap-spring mechanism.

6. A surgical suturing device according to claim 1, wherein said control plate and said base plate are coupled by a coil spring which extends parallel to said two plates and biases said two plates in the opening direction of said handle.

7. A surgical suturing device according to claim 1, wherein said suturing head includes a stationary jaw and a movable jaw.

8. A surgical suturing device according to claim 7, wherein said needle is locked in said stationary jaw by said control rod when said control rod is received in the recess in the respective needle end and is held in said movable jaw by a spring-loaded pin which is received in the respective needle recess and held therein by said spring with an adjustable force so selected that the needle can be engaged and disengaged without being damaged.

9. A surgical suturing device according to claim 1, wherein said suturing head includes two movable jaws in each of which said needle is engageable at opposite ends by a control pins operable by said control rods.

10. A surgical suturing device according to claim 9, wherein said control pins each have an end of increased thickness disposed in an increased diameter portion of a bore receiving said control pin, and slide control members are provided which have curved end faces with which said ends of increased thickness of said control pins are engaged by springs disposed in said increased diameter portions of said bores, said curved end faces having a center of curvature coinciding with the pivot axis of said jaws such that the axial position of said control pins is not affected by the angular position of said jaws.

11. A surgical suturing device according to claim 10, wherein said control rods have at their distal ends parts which are connected to said slide control members by an intermediate spring.

12. A surgical suturing device according to claim 1, wherein said needle is triangular in cross-section.

13. A surgical suturing device according to claim 12, wherein said needle has oppositely pointed tips with the eye disposed in the center, a flat back portion in the center of the needle and ledges in the area between the center and the tips.

14. A surgical suturing device according to claim 13, wherein said needle tips have flat inclined areas for improved insertion of the needle tips into the needle guides.

15. A surgical suturing device according to claim 12, wherein said needle is triangular in cross-section.

16. A surgical suturing device according to claim 15, wherein said recess adjacent the needle tip is cylindrical in shape.

17. A surgical suturing device according to claim 15, wherein said recess adjacent the needle tip is prismatic in shape.

* * * * *